(12) United States Patent
Gardiner

(10) Patent No.: US 6,732,457 B2
(45) Date of Patent: *May 11, 2004

(54) REHABILITATIVE SHOE INSOLE DEVICE

(75) Inventor: Roy J.W. Gardiner, Richmond Hill (CA)

(73) Assignee: Barefoot Science Technologies Inc, Richmond Hill (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/942,972

(22) Filed: Aug. 31, 2001

(65) Prior Publication Data

US 2002/0014024 A1 Feb. 7, 2002

Related U.S. Application Data

(63) Continuation-in-part of application No. 09/243,457, filed on Feb. 3, 1999, now Pat. No. 6,301,807, which is a continuation-in-part of application No. 08/994,500, filed on Dec. 24, 1997, now abandoned.

(51) Int. Cl.$^7$ ............................. A61F 5/14; A43B 13/40
(52) U.S. Cl. ................... 36/155; 36/43; 36/44; 36/27; 36/158
(58) Field of Search ........................ 36/155, 43, 44, 36/27, 158, 168, 173, 179, 91

(56) References Cited

U.S. PATENT DOCUMENTS

| | | | | |
|---|---|---|---|---|
| 788,469 A | * | 4/1905 | Huether | 36/155 |
| 1,136,443 A | * | 4/1915 | Scholl | 36/155 |
| 1,142,849 A | * | 6/1915 | Scholl | 36/165 |
| 1,346,059 A | * | 7/1920 | Robson et al. | 36/158 |
| 1,378,398 A | * | 5/1921 | Block | 36/159 |
| 1,804,549 A | * | 5/1931 | Temler | 36/158 |
| 1,924,792 A | * | 8/1933 | Kay | 36/155 |
| 2,157,454 A | * | 5/1939 | Keys | 36/165 |
| 2,510,654 A | * | 6/1950 | Pepin | 36/155 |
| 2,613,455 A | * | 10/1952 | Amico | 36/155 |
| 5,404,659 A | * | 4/1995 | Burke et al. | 36/43 |
| 5,438,768 A | * | 8/1995 | Bauerfeind | 36/44 |
| 6,301,807 B1 | * | 10/2001 | Gardiner | 36/155 |

FOREIGN PATENT DOCUMENTS

CH 83595 * 12/1919

* cited by examiner

*Primary Examiner*—Ted Kavanaugh
(74) *Attorney, Agent, or Firm*—Gowling Lafleur Henderson, LLP; Peter Milne

(57) ABSTRACT

An insole device configured to fit the profile of the human foot to promote proprioceptive stimulation of the Golgi tendon organ. The midfoot section of the insole device has an asymmetric domed structure that is presented to the plantar aspect of the foot at a location found to be the anatomical apex of the foot's arch system. The asymmetric domed structure displays physical properties to catalyst muscle group balancing by using the body's proprioceptive feedback mechanisms. The asymmetric domed structure displays physical properties such that it does not provide functional bracing or support to the plantar aspect of the foot. The net result will be more structurally sound foot capable of more energy efficient and less injury inducing use. The plantar aspect of the insole or midsole device is characterized by a dominant cavity having the ability to receive and interchange the biofeedback catalyst and the many forms therefore, as well as being characterized by provisions to ensure proper and permanent placement of the catalyst.

14 Claims, 12 Drawing Sheets

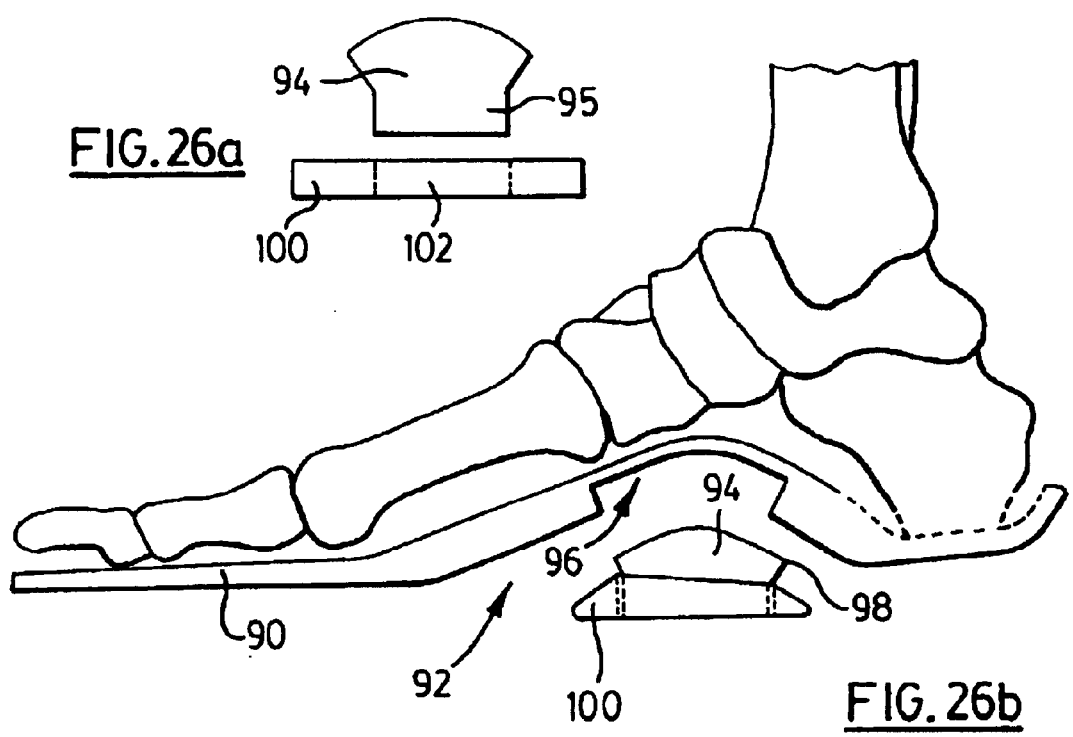
FIG. 26a
FIG. 26b
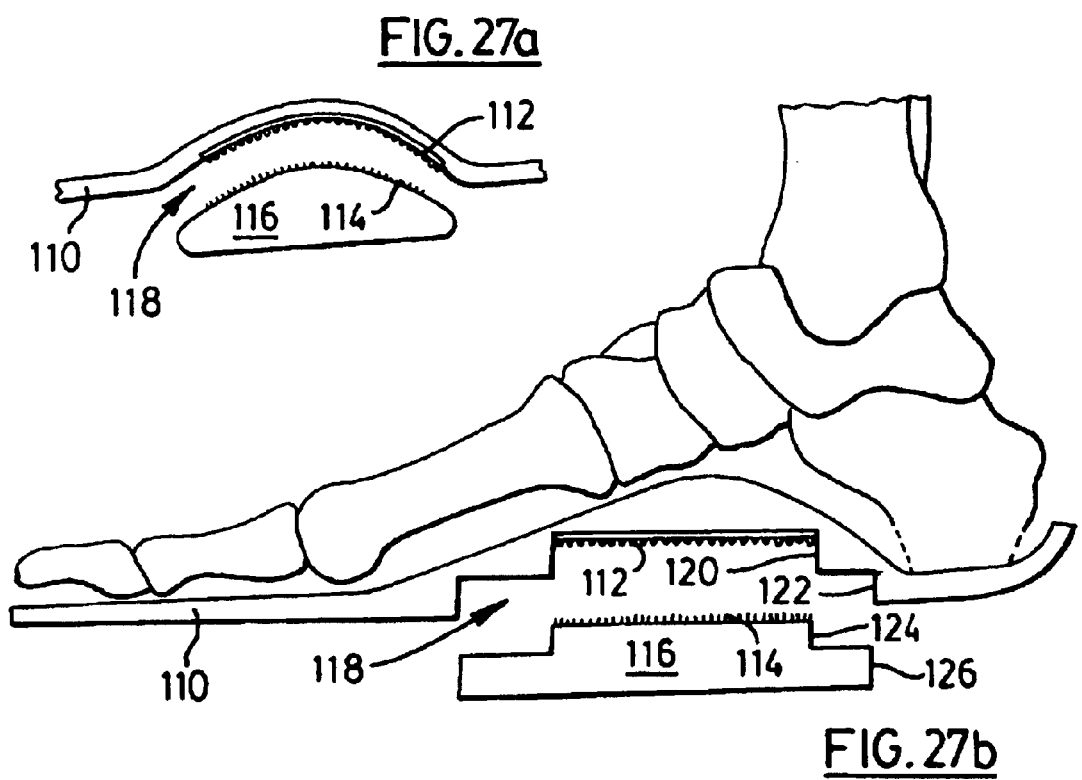
FIG. 27a
FIG. 27b

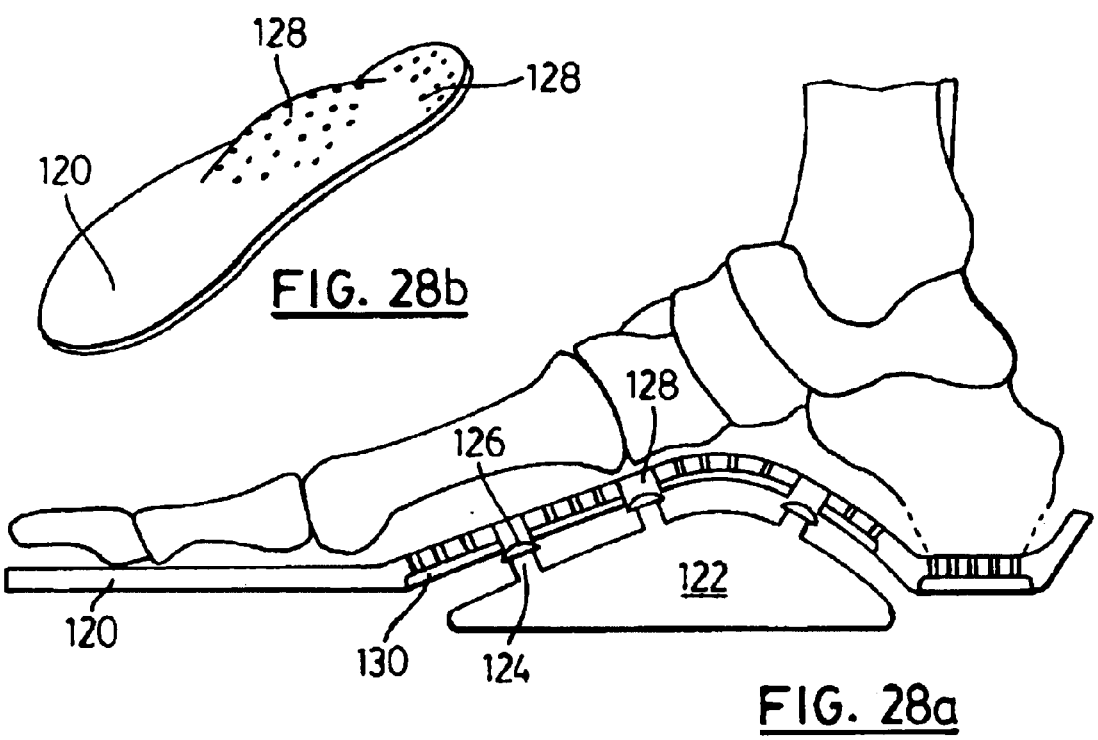
FIG. 28b
FIG. 28a
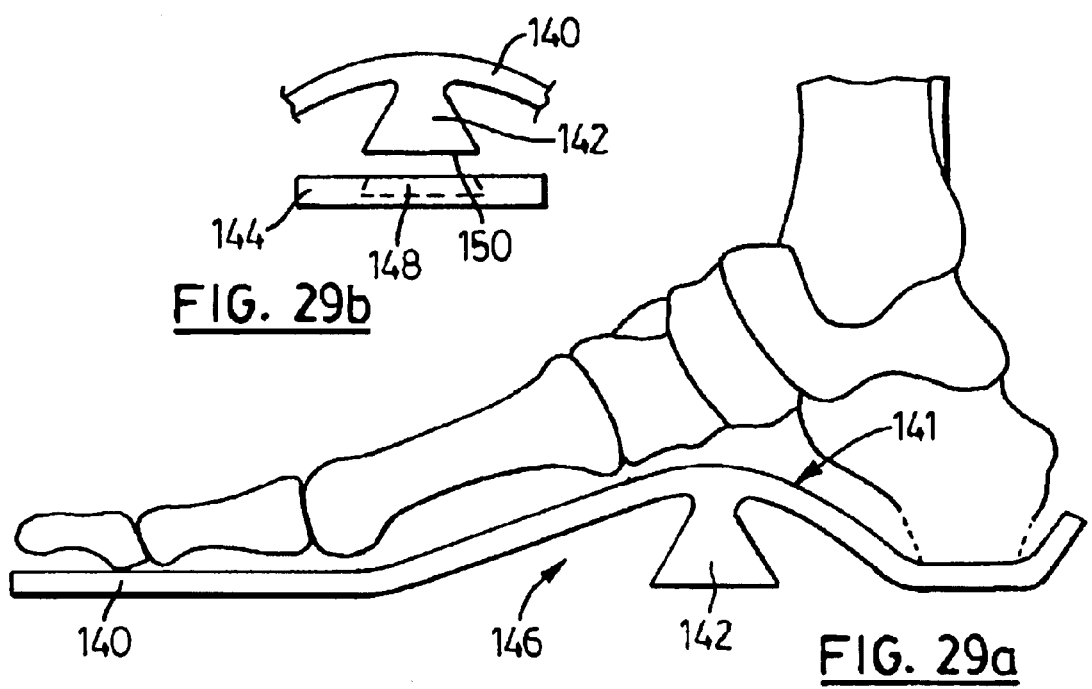
FIG. 29b
FIG. 29a

REHABILITATIVE SHOE INSOLE DEVICE

This application is a continuation-in-part of U.S. patent application Ser. No. 09/243,457 filed Feb. 3, 1999 now U.S. Pat. No. 6,301,807, which was a continuation-in-part of U.S. patent application Ser. No. 08/994,500 filed Dec. 24, 1997 now abandoned.

FIELD OF THE INVENTION

The present invention relates to an insole for a shoe. In particular, the present invention relates to an insole device that can rehabilitate a foot by stimulating a proprioceptive response in the wearer's foot.

BACKGROUND OF THE INVENTION

Professionals dealing with gait related pathologies generally accept that a large majority of persons will, at some time in their lives, suffer some form of gait related pain or dysfunction. It is also well accepted that, in the majority of cases, the mechanism underlying the pathology, injury, or dysfunction is biomechanically related to the interface between the foot and the ground, during the support phase of the gait cycle.

It has been proposed that providing a device to create a proprioceptive, or internal, feedback stimulus to a wearer's foot can directly target the underlying pathology, injury or dysfunction. Such a device is disclosed in U.S. Pat. No. 5,404,659 to Burke et al. As disclosed in U.S. Pat. No. 5,404,659, an arch rehabilitative catalyst stimulates the Golgi tendon organ, which in turn, stimulates the musculoskeletal structure of the foot to rehabilitate the foot structure. The catalyst is an asymmetrically domed hump, which creates a mild to strong discomfort to initially stimulate the Golgi tendon organ.

However, it has been found that the device disclosed in U.S. Pat. No. 5,404,659 does not function as described, and that the majority of wearers find the device too uncomfortable to use. In particular, when subjected to conventional vertical compressive forces of a person walking in the range of 2.5 times body weight, the device is designed to deflect between 40% and 60% of its maximum height, and when subject to only one times a person's weight, there should be no deflection. Rather than stimulate the Golgi tendon organ to create a proprioceptive response, deflections in this range can cause severe pain to a wearer, as there is insufficient give, and the wearer is always aware of the presence of the device. In addition, as disclosed in U.S. Pat. No. 5,504,659, the device has an ideal apex height of 5.25% to 7.6% of the total foot length. A device build according to these dimensions results in an overly high arch height, and can cause severe discomfort, and possible injury, to a wearer. It is further disclosed that the absolute, non-weight bearing height of the device should be the same regardless of body weight and arch height. This is clearly wrong, since different wearers will have different comfort thresholds and arch heights.

In general, the device disclosed in U.S. Pat. No. 5,404,659 does not function as described. Wearers would find the device too hard to use successfully, and rather than stimulating a proprioceptive response, the device would cause pain and discomfort at each step. The pain engendered in the foot of a wearer would, in fact, cause the wearer to limit the pressure applied to the foot to avoid the discomfort, rather than exercising the foot by creating an imperceptible simulation as is its stated goal.

SUMMARY OF THE INVENTION

A rehabilitative insole device is provided which has a substantially dome-shaped catalyst for interfacing with the plantar aspect of a human foot. The catalyst has an apex for aligning with a target area within the foot, the target area being defined by the point of articulation of the lateral cuneiform, cuboid and navicular bones of the foot to permit unhibited triplanar pivoting of the foot about the target area. The catalyst has a maximum height at the apex of from 1% to 5% of the length of the foot, wherein the length of the foot corresponds substantially to the length of the rehabilitative insole device. The catalyst is resiliently deformable to apply an upwardly directed pressure to stimulate the Golgi tendon organ in the foot in response to downward pressure on the catalyst by the foot. The resilient member has a resilient deformability to allow the catalyst to deflect from between 40% and 100% of the maximum height in response to vertical forces of a person standing at rest being applied to the catalyst.

The catalyst may have a cavity for removably accommodating an insert which acts between the catalyst and an underlying surface to control the resilient deformability of the catalyst. The catalyst and the insert may have co-operating engagement means for securing the insert to the insole. The co-operating engagement means may include detent means for resisting separation of the insert from the insole and lateral shifting therebetween.

The detent means may include an enlarged end on one of the insert and the catalyst which is insertable through a narrower opening in the other of the insert and the catalyst.

The enlarged end may be provided on a distal end of at least one projection entending from a respective of the insert and the catalyst.

The catalyst may have an outer cover over the insole with at least one projection extending from the outer cover through the insole.

The co-operating engagement means may include vertical walls on the insert which register with corresponding vertical walls on the receptacle to resist lateral shifting therebetween. The detent means may include mating strips of hook and loop fastener secured to an inner lateral surface of the receptacle and an outer lateral surface of the insert.

The projection may be a resilient column depending from the catalyst through the receptacle and the insert may have a recess which closely surrounds at least part of the column to resist deformation of the column in a lateral direction thereby enhancing the stiffness of the resilient column.

A magnetic material may be interspersed between the insole and the insert.

The insert may have a resilient column extending downwardly from the insole in the cavity and a detachable ring member for receiving the column and resisting resilient deformation of the column in the lateral direction, thereby enhancing the stiffness of the resilient column.

The co-operating engagement means may be mating strips of hook and of loop fastener secured to registering faces of the insert and the insole.

The co-operating engagement means may include respective strips of opposite pole magnetic material secured to registering faces of the insert and the insole. The co-operating engagement means may further include vertical walls on the insert which register with vertical walls on the receptacle to resist lateral shifting therebetween.

The detent means may include a plurality of projections extending upwardly from the insert and terminating in enlarged ends. The detent means may also include apertures through the catalyst for receiving the projections with the enlarged ends terminating above the catalyst once the insert is secured to the insole. The apertures and projections may be arranged in a pattern corresponding to reflexology points on the foot to apply reflexology therapy in response to downward pressure by the foot on the insole. A magnetic material may further be provided between the insole and the insert around the projections. dr

DESCRIPTION OF THE DRAWINGS

Preferred embodiments of the present invention will now be described, by way of example only, by reference to the attached drawings, in which:

FIGS. 26a and 26b illustrate yet another receptacle/insert configuration;

FIGS. 27a and 27b illustrate insert/receptacle configurations using a hook and loop fastener as a cooperating engagement means;

FIGS. 28a and 28b correspond to the FIG. 25a embodiment but also illustrate the incorporation of magnetic foil;

FIGS. 29a and 29b illustrate an insole cavity having a downwardly protruding pillar and a detachable ring member.

DETAILED DESCRIPTION

Figure 1:
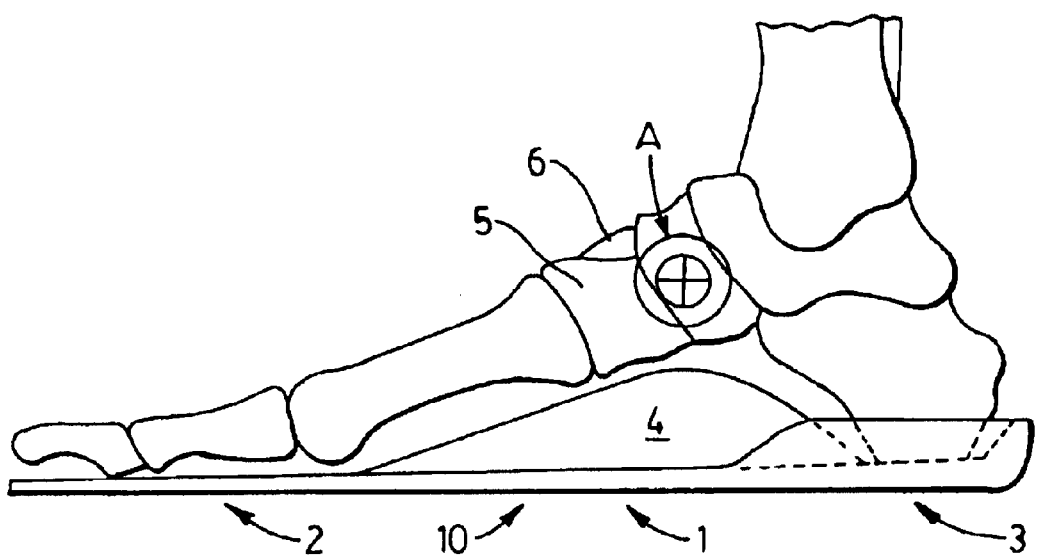
FIG. 1 is a medial sagittal view of an insole showing the location of an arch rehabilitative catalyst relative to foot placement on the insole or midsole.
Figure 2:
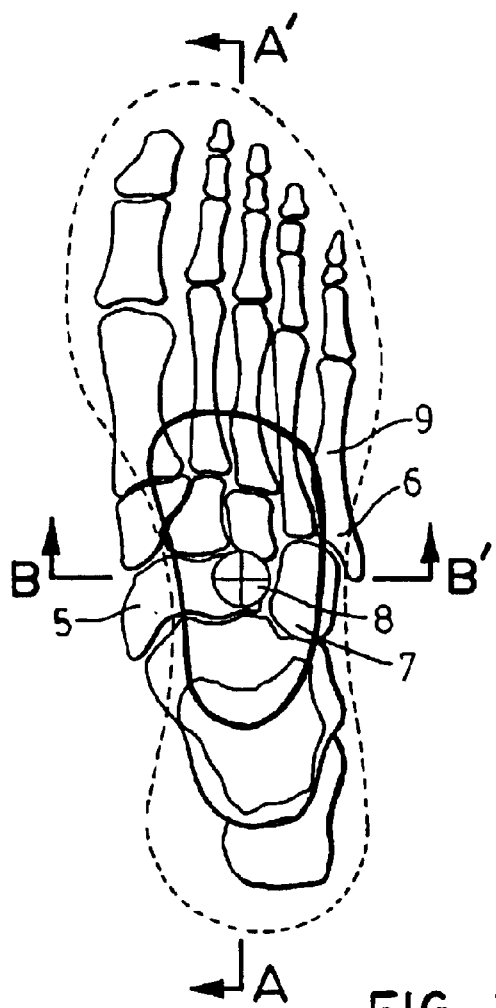
FIG. 2 is a dorsal view of an insole showing the location of an arch rehabilitative catalyst relative to foot placement.

Referring to FIGS. 1 and 2, an insole or midsole device 1 is shown. Device 1 has a dorsal surface contacting the underside of a foot. A proprioceptive catalyst 4 is located in the midsection of device 1, substantially aligned with the apex of the foot's arch system. The apex of the arch system is shown at the target area "A" shown in FIGS. 1 and 2, and is defined as the intersection of the navicular 5, lateral cuneiform 6, and the cuboid 7 bones, or slightly medial thereof. As will be understood by those of skill in the art, a wearer's foot comprises the bones of the foot, interconnected by ligaments. A layer of muscle is attached to the bones by tendons, and covered by a thick layer of fat tissue which is finally covered by a layer of skin.

The proprioceptive catalyst 4 has an area and perimeter 9 defined by an anterior arc, a posterior arc, a medial arc, and a lateral arc. Preferably, the anterior arc has its maximum point lateral to the $2^{nd}$ metatarsal and medial to the $3^{rd}$ metatarsal, and does not extend in an anterior direction more than 70% of the total foot length, nor less than 60%; the posterior arc has its maximum point medial to the lateral tubercle of the calcaneus and lateral to the medial tubercle, and does not extent in a posterior direction at any point less than 15% of the foot's total length or greater than 25% of the foot's total length; the medial and lateral arcs do not exceed the medial and lateral boundaries created by the foot itself; and the proprioceptive catalyst 4 is entirely within the periphery set by the metatarsal heads, calcaneus, and lateral and medial borders of the foot.

Proprioceptive catalyst 4 is an asymmetric dome with its apex aligned with target area "A", as described above, when viewed from where from a sagittal plane. The height the catalyst 4 at the apex should ensure that, when a user is at rest, target area "A" is at a height between 5.28% and 7.6% of the foot's total length. The present inventor has found that this corresponds to an actual catalyst height of in the range of 1% to 5% of the foot's length, with an ideal ratio of approximately 3.6% of a wearer's foot length.

Preferably, catalyst 4 should be manufactured in such a fashion, and of such a material, that it displays certain preferred compression and rebound characteristics. For example, when the catalyst is subjected to the vertical forces of a person standing at rest, the catalyst will display a deflection between 40% and 100% of its maximum height.

Figure 3:
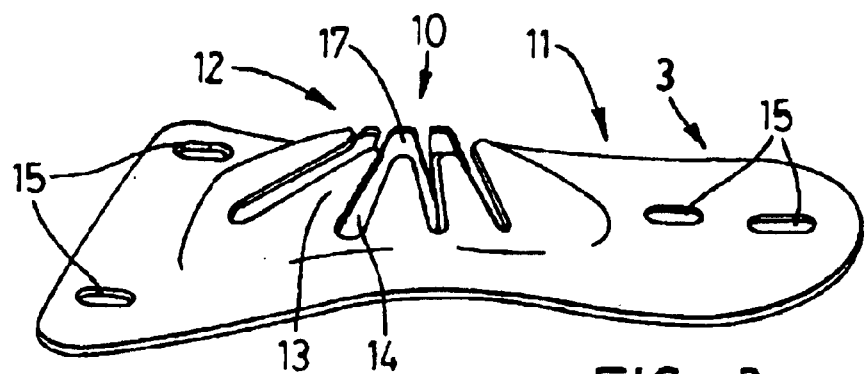
FIG. 3 is a perspective view of a cantilever spring device of the present invention showing an undercarriage and positioning apertures.
Figure 4:
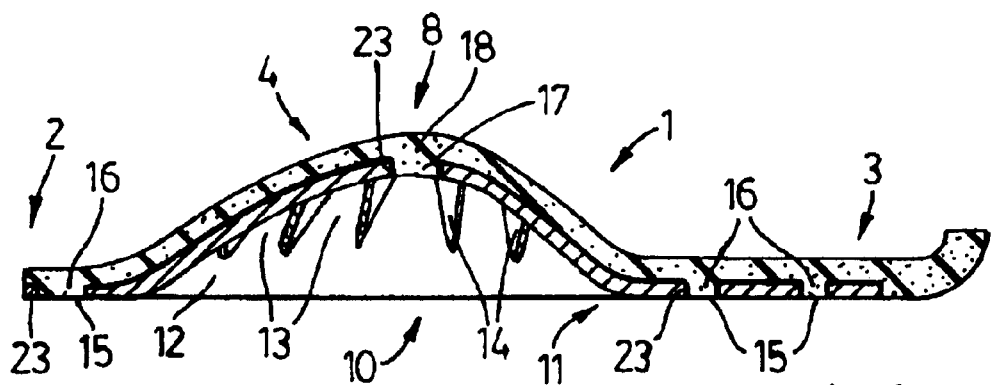
FIG. 4 is a sagittal plane cross-sectional view of the insole or midsole and the cantilever spring device of FIG. 3, through section A–A' of FIG. 2.
Figure 6:
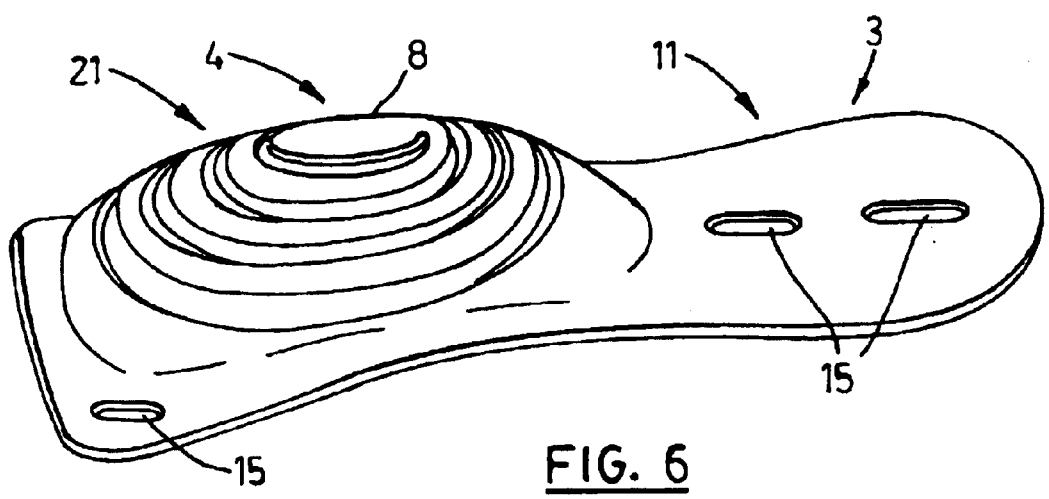
FIG. 6 is a perspective view of another embodiment utilizing a domed shaped coil spring device of the present invention showing an undercarriage and positioning apertures.
Figure 7:
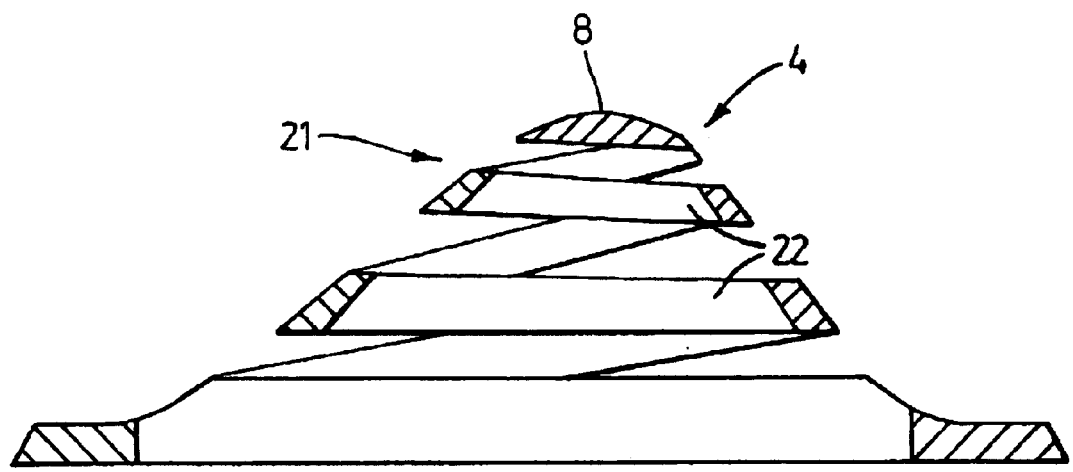
FIG. 7 is a frontal plane cross-sectional view of further embodiment of a domed shaped coil spring device of the present invention through section B–B' of FIG. 6.

A first embodiment of the present invention is shown in FIGS. 3 and 7. Referring to FIG. 3 and 4, the device 1 interfaces with an undercarriage 11 from a sagittal plane view through section A–A'. Undercarriage 11 has a heel region 3 and midfoot region 10. The midfoot region 10 defines a catalyst 4 supported by a resilient member in the form of a domed cantilever spring device 12. Cantilever legs 13 flex and compress into voids 14, thereby allowing compression of the legs 13 without the legs 13 interfering with each other during compression. The apex 8 of the catalyst, in the form of a cantilever spring device 12 provides a positioning aperture 17 aligned with a positioning pin 18 in the device 1. Positioning apertures 15 are also aligned with positioning pins 16 of the device 1 to ensure the proper placement and maintenance of placement of the catalyst 4 and its apex 8. Vertical side walls 23 of the positioning pins 16 and the positioning apertures 15 act to prevent anterior/posterior and medial/lateral shifting of the inserted mechanism as provided in FIGS. 3, 4, 5 and 6. The apertures 15 and corresponding placement pins 16 can be located at any location on the device 1 and the undercarriage 11 as seen fit by design and functionality. Differences in body weight, activity and foot type can be compensated for by the selection of materials for the fabrication of the undercarriage 11 and the cantilever spring device 12, or the thickness of the undercarriage 11 and the cantilever spring device 12. The undercarriage 11 and the cantilever spring device 12 can be formed through injection moulding or vacuum forming and stamping. Polymers such as Delrin, Hytrel and Zytel from E. I. DuPont, PVC, Pebax or layered fabric and resin combinations such as fibreglass or graphite can provide the desired physical and material properties.

An advantage of device 1 is the high flex fatigue characteristics of the materials of choice. This will enable the device 1, and in particular the catalyst 4, to be used for much longer periods of time than that disclosed in other shoe insole or midsole units that utilize proprioceptive feedback mechanisms in the human body to increase the structural integrity of the human foot. The desired regulation of the vertical maximum distance from the supporting surface of the device 1 to the apex 8 of the catalyst 4 occurs as forces are applied vertically to the cantilever mechanism at its apex 8.

Figure 5:
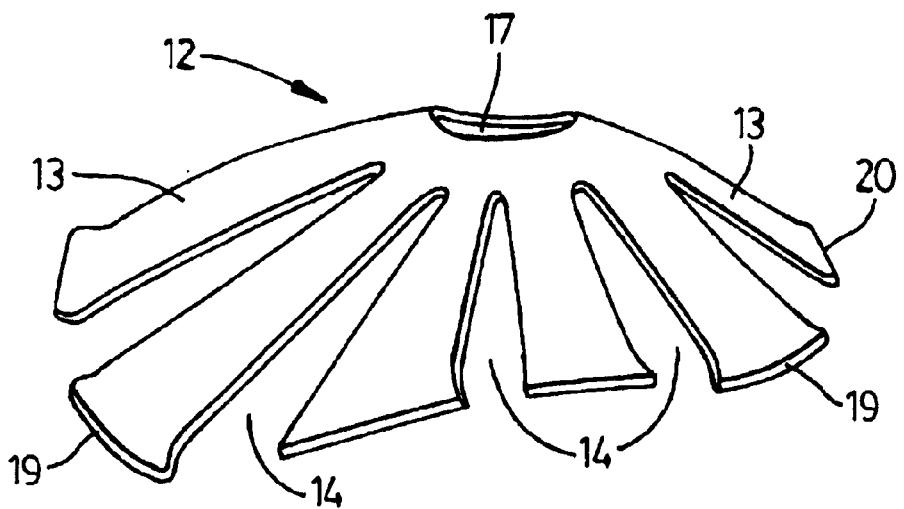
FIG. 5 is a perspective view of an alternative embodiment of the cantilever spring device of the present invention to be designed into the undercarriage.

FIG. 5 illustrates an alternative design to the cantilever spring device 12 where the legs 13 of the cantilever spring device 12 deflect and move away from the centre region. A rear finger 20 on the spring device 12 in FIG. 5 can be molded as an integral part of the undercarriage 11 or permanently affixed to an undercarriage 11. Each leg 13 of the cantilever spring device 12 has a foot 19 that permits it to smoothly elongate without becoming obstructed by friction between the lower surface of the foot 19 and the layer of the inside of the shoe with which it is in contact. This embodiment as illustrated in FIG. 5, also incorporates positioning pins 18 and 16, and positioning apertures 15 and 17 and their inherent vertical sidewalls 23 to ensure the proper placement of the catalyst 4 and its apex 8 which maintains the catalyst in its position.

FIG. 6 shows a further configuration for the resilient member supporting catalyst 4 of the present invention. It involves the incorporation of a coiled spring device 21 to be aligned to the target area of the apex 8 of the foot's arch system as defined and to be affixed to or designed as an integral part of the undercarriage 11. This is illustrated in FIG. 6 where a perspective view of the coiled spring device 21 is shown. Again the incorporation of positioning pins 16 and the positioning apertures 15 and the vertical sidewalls 23 created therein prevent any medial/lateral and anterior/posterior shifting of the mechanism and ensure its proper placement.

It is believed that the specific characteristics that are desired for the cantilever spring mechanisms of the present invention can be attained in at least two different ways. The first of these is to use the design, particularly the design characteristics of the legs 13 as a constant, and adopt different grades of the aforementioned polymers, or similar. The calculation of the vertical force being applied and the use of trigonometry will allow the simple calculation of the force vector representing that going down the legs 13, and this can be used to determine the desired polymer, or grade of polymer, based on its flex modulus: F=(KX); where F is the force being applied vertically at the apex 8, K is the spring constant which can be provided through the flex modulus, and X is the distance that the spring changes in length, in this case the difference between the resting height "H+X" and the height "H" when the cantilever is compressed through the application of a vertical force applied at the target area.

The second method of attaining the desired rebound and compression characteristics would be to hold the polymer of choice as a constant and alter the thickness of the legs 13 as shown in FIGS. 3, 4 and 5. The use of the flex modulus information, relative to material thickness, will be able to provide the necessary information as to determine the ideal material thickness. The benefit of this, is its ability to provide a variable deflection rate. That is the cantilever mechanism 12 can be designed to react equally efficiently when subjected to varying forces through varying thickness of the legs 13. An example of which is the integration of thicker legs 13 if the application is such that it provides an activity or an environmental stress characteristic of greater vertical loading, such as the activity of basketball compared to walking, or a 150 kg athlete compared to an 80 kg athlete, both having the same shoe size.

The benefits of the improved rehabilitative catalyst of the present invention are generally threefold. First, the position pins 16 and the positioning apertures 15 and their complimentary vertical sidewalls 23 ensure the proper placement of the catalyst 4 and the maintenance of the placement. Second, by properly integrating a resilient member with the polymers and materials of choice as discussed, the catalyst is capable of showing extremely high durability characteristics. Third, the resilient member can be designed to obtain the desired compression and spring characteristics required for a particular application. The maintenance of these properties is beneficial because:

(i) The rebound characteristics ensure that the catalyst 4 will return to its original apex height 8, thereby ensuring contact with the apex of the foot's arch system. This contact provides a catalyst to stimulate the proprioceptive mechanism necessary for the proper restructuring of the foot's arch systems' musculoskeletal characteristics.

(ii) The compression characteristics allow the human foot's arch system to deflect in a natural manner and thereby the human arch system can act as a natural cushioning mechanism. This also prevents any bracing effects from occurring.

(iii) The compression characteristics allow the human foot arch system to deflect in a natural manner thereby allowing eccentric contractions of the foot's plantar musculature to occur. This regulates the velocity of arch deflection as well as allows the series and parallel spring characteristics of the muscle to store energy and contribute that stored energy to effective propulsion.

In another aspect of the invention it is desirable to redesign the geometric nature of the plantar aspect of the device 1 in the region of the catalyst 4 to facilitate the easy removal and insertion of an appropriately shaped resilient member 26, as per a few of the options presented in FIGS. 10, 13, 16, and 17, to provide the necessary rebound, compression and deflection traits necessitated by the wearer and to provide vertical walls 25 and 31 thereby ensuring proper positioning of the resilient member 26 and catalyst and to ensure the proper maintenance of the desired position. The insertable resilient member 26 allows for customization of the catalyst in the same manner as discussed with reference to the legs 13 of the spring device. The resilient member 26 can be provided in a variety of foam type materials of a variety of heights, hardnesses and compression sets to address body weight requirements, foot type characteristics, or activity of usage.

Previous inventions have featured a catalyst having a receptacle in the form of a cavity having no vertical walls to ensure proper positioning of the filler object or insert 26 or mechanism and to ensure the proper maintenance of the desired position.

The removal and insertion of resilient members into the aforementioned curvilinear cavity has revealed two shortcomings, the first of these was that when a lower strength adhesive system was used that facilitated the ease of removal and insertion of the resilient member the resilient member was predisposed to shift out of position when subjected to the medial/lateral shearing forces that are characteristic of normal gait. This shifting prevented the resilient member from being maintained in the desired position as outlined.

The second shortcoming was evident when an adhesive system of adequate strength was used to ensure the positional maintenance of the resilient member. The adhesives used proved to display tensile strength properties far in excess of the surrounding device 1 material and the resilient member. Attempts to dislodge the resilient member for the purpose of inserting a newer resilient member as necessitated by the foot restructuring initiated by the invention, proved to cause substantial damage to the device 1 material to the extent rendering the device 1 unusable.

FIGS. 8 through 19 reveal options that are available with respect to the redesign of a system that ensures the proper placement of the resilient member 26, the maintenance of that placement and the easy removal and insertion of the resilient member 26.

Figure 8A:
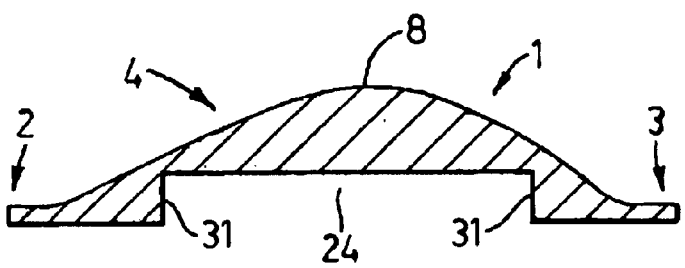
FIGS. 8a and 8b are frontal and sagittal plane cross sectional views of the insole or midsole through sections A–A' and B–B' of FIG. 2 showing the positioning of a rectangular receptacle cavity in the area of the arch rehabilitative catalyst, respectively.
Figure 8B:
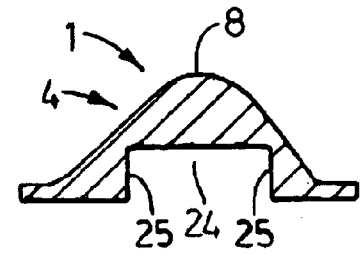
Figure 9:
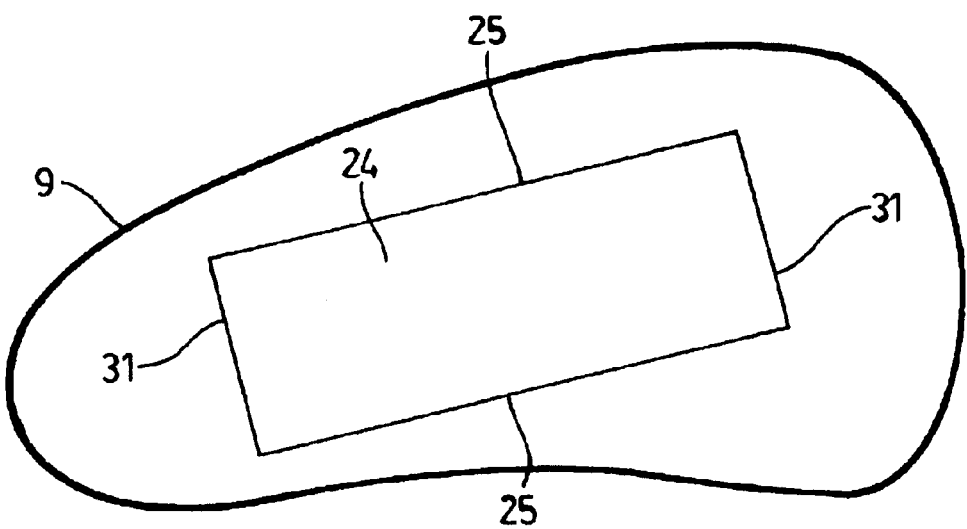
FIG. 9 is a plantar aspect view of the arch rehabilitative catalyst and the rectangular receptacle cavity in the arch rehabilitative catalyst shown in FIGS. 8a and 8b.
Figure 10:
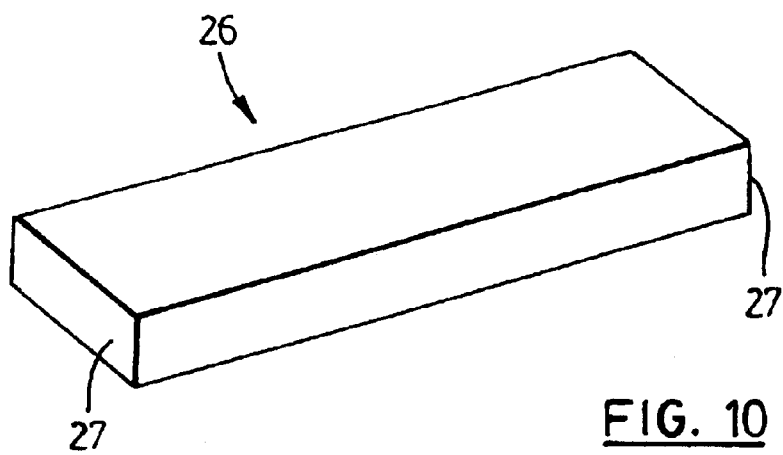
FIG. 10 is a perspective view of an insert that can be inserted into the rectangular receptacle cavity in the arch rehabilitative catalyst.

FIGS. 8 through 10 reveal an device 1, with a forefoot region 2, a heel region 3 and with an catalyst 4 with a distinct apex 8, the target area aligned with the anatomical region encompassing the intersection of the navicular 5, lateral cuneiform 6, and the cuboid 7 bones. The plantar surface of the device 1 in the region set forth by the boundaries of the catalyst 4 is characterized by a geometric cavity 24. The cavity displays vertical walls 25 for resisting medial-lateral shifting of the resilient member 26 and vertical walls 31 for resisting anterior-posterior shifting of the resilient member 26. The preferred embodiment as detailed in FIGS. 8 through 10 reveal a geometric cavity 24 of a rectangular nature and a resilient member 26 of a corresponding rectangular nature with vertical side walls 27 designed to engage with the vertical sidewalls 25 and 31 of the cavity 24.

Figures 11A, 11B:
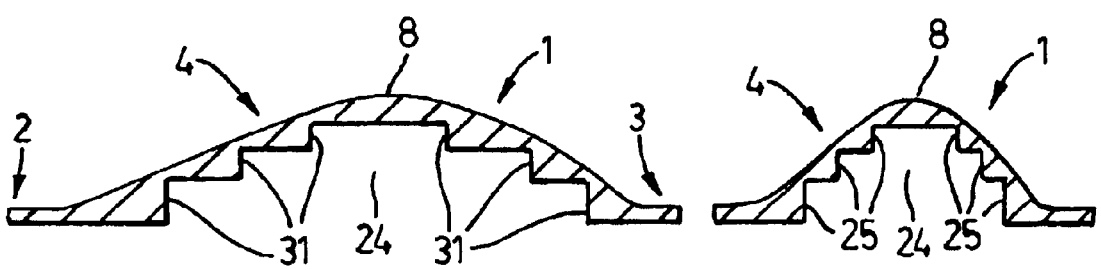
FIGS. 11a and 11b are frontal and sagittal plane view of further embodiment of the insole or midsole through sections A–A' and B–B' of FIG. 2 showing the positioning of a rectangular pyramidal receptacle cavity in the arch rehabilitative catalyst.
Figure 12:
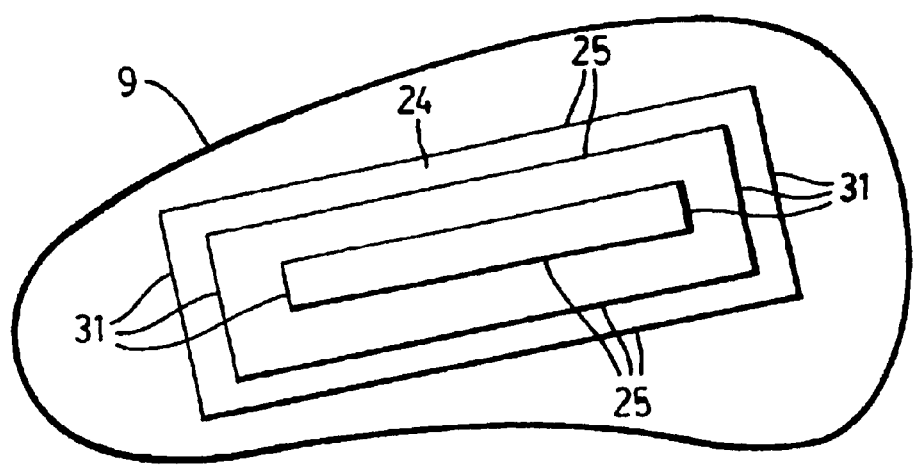
FIG. 12 is a plantar aspect view of the arch rehabilitative catalyst and the rectangular pyramidal receptacle cavity in the arch rehabilitative catalyst shown in FIGS. 11a and 11b.
Figure 13:
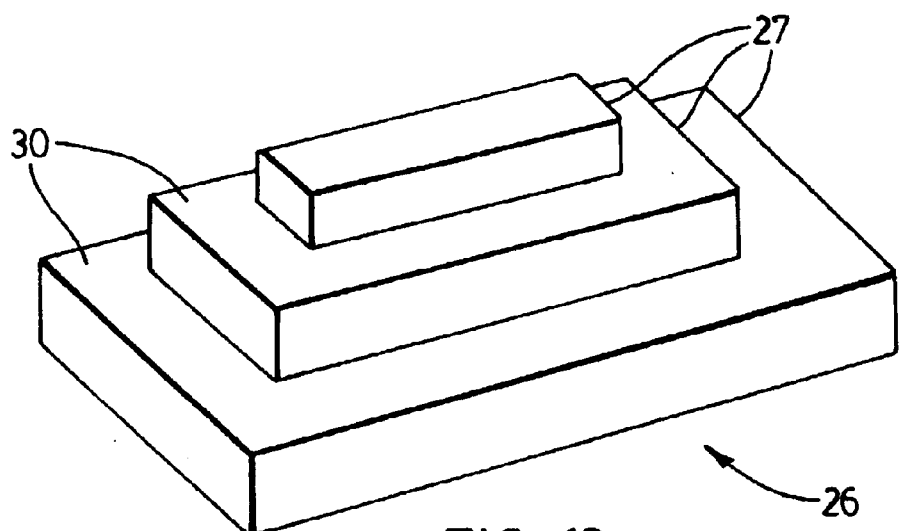
FIG. 13 is a perspective view of an insert that can be inserted into the rectangular pyramidal receptacle cavity in the arch rehabilitative catalyst.

FIGS. 11 through 13 show a device 1, with a forefoot region 2, a heel region 3 and with a catalyst 4 with an apex 8, the apex aligned with a target area in the foot defined by the anatomical region encompassing the intersection of the navicular 5, lateral cuneiform 6, and the cuboid 7 bones. The plantar surface of the device 1 in the region set forth by the boundaries of the catalyst 4 is characterized by a geometric cavity 24. The cavity displays vertical walls 25 for engaging with vertical sidewalls 27 of the resilient member 26 for resisting medial-lateral shifting of the filler resilient member 26 and vertical walls 31 for engaging with the vertical sidewalls 27 of the resilient member 26 for resisting anterior-posterior shifting of the resilient member 26. The preferred embodiment as detailed in FIGS. 11 through 13 reveals a geometric cavity 24 of a pyramidal stacked rectangular nature and a resilient member 26 of a corresponding pyramidal stacked rectangular nature. In reference to this configuration it is possible to have the rectangular layers 30 each as an insatiable filler object or insert layer and therefore each of a different material and/or differing material properties. In this manner the variable rate deflection concept outlined earlier can be attained while maintaining and ensuring the proper positioning of the catalyst 4, apex 8 and the resilient member 26. This variable deflection benefit an also be achieved through the method as provided in FIGS. 8 through 10 by allowing the resilient member 26 to be constructed through the application of stacked layers where each layer is capable of displaying individual deflection, compression and rebound characteristics.

Figures 14A, 14B:
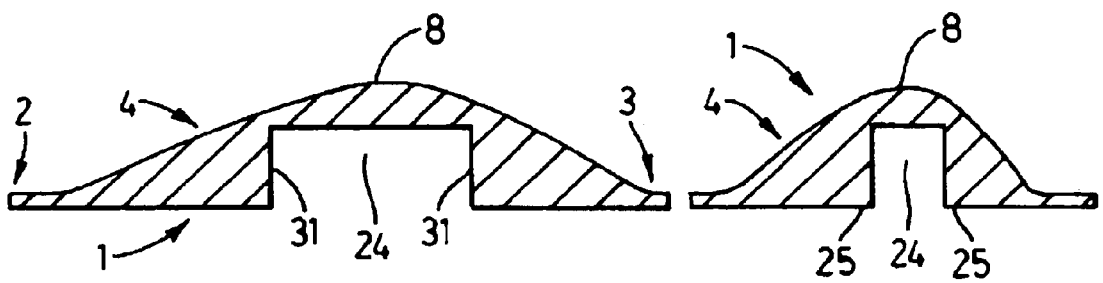
FIGS. 14a and 14b are frontal and sagittal plane views of another embodiment of an insole through sections A–A' and B–B' showing the positioning of a rectangular receptacle cavity with curvilinear ends in the arch rehabilitative catalyst.
Figure 15:
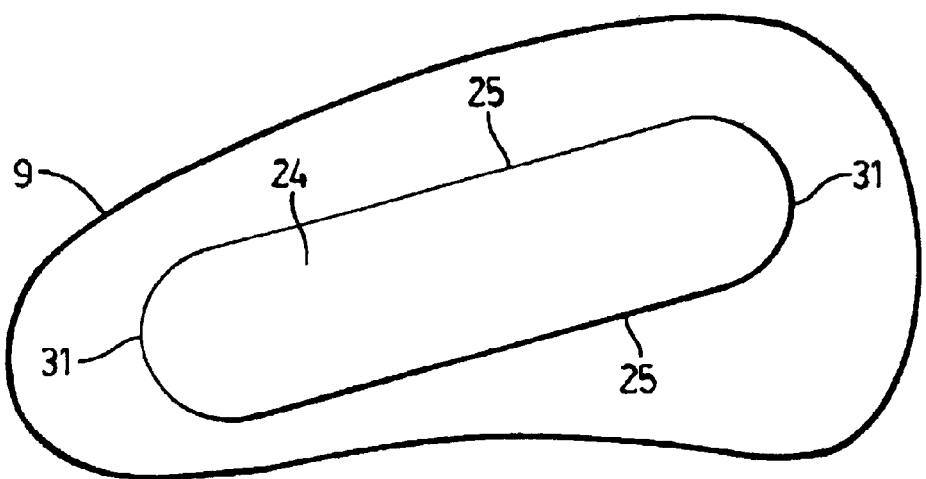
FIG. 15 is a plantar aspect view of the arch rehabilitative catalyst and the rectangular receptacle cavity with curvilinear ends in the arch rehabilitative catalyst shown in FIGS. 14a and 14b.
Figure 16:
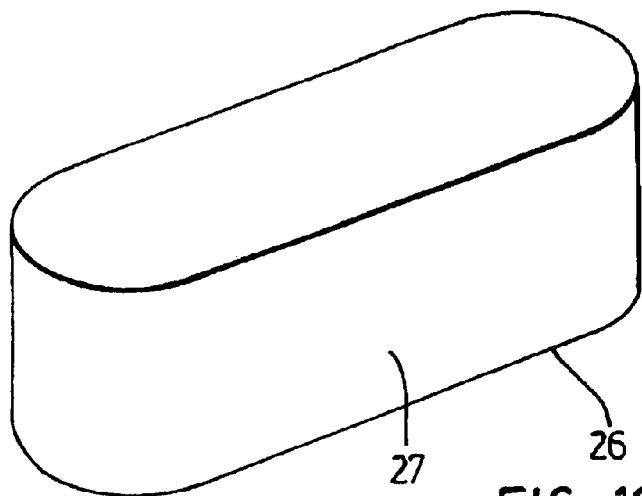
FIG. 16 is a perspective view of an insert that can be inserted into the rectangular receptacle cavity with curvilinear ends in the arch rehabilitative catalyst shown in FIGS. 14a and 14b.

FIGS. 14 through 16 display a geometric configuration consistent with FIGS. 8 through 10 with the exception of the anterior and posterior most ends of the resilient member 26, and the anterior and posterior walls of the geometric cavity 24, are curvilinear in nature.

The geometric cavity 24 can also be designed to facilitate the insertion of an appropriately matching shaped resilient member other than of foam type material providing the desired rebound, deflection and rebound characteristics. The resilient member can take the form of a compressive mechanical system such as coil spring devices, bi-valve spring devices, cantilever spring devices, or fluid filled structures, including gas filled structures. The resilient member is designed to fill the geometric cavity 24 such that the vertical sidewalls 25 and 31 of the geometric cavity 24 engage the resilient member and ensure the proper and permanent placement of the resilient member. The compressive nature of the resilient member can be linear in nature or can provide a variable rate of deflection.

Figure 17:
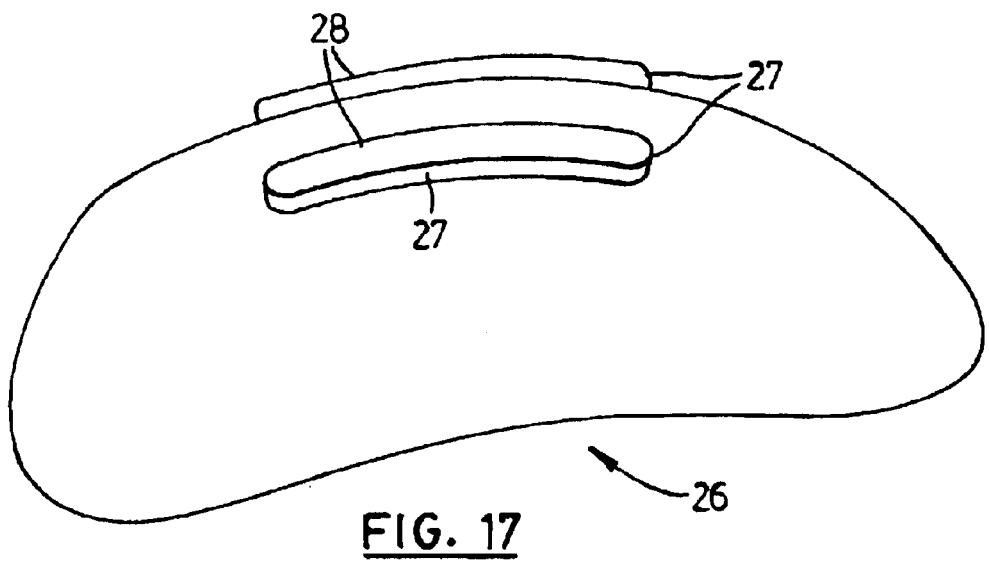
FIG. 17 is a perspective view of further embodiment of a domed shaped insert with positioning and security ribs on its dorsal aspect.
Figure 18:
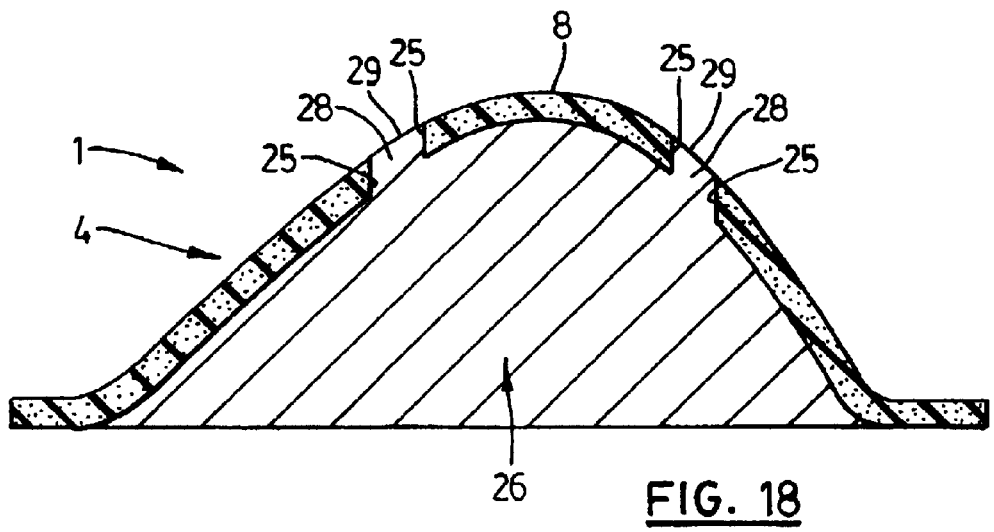
FIG. 18 is a frontal cross-sectional view of the arch rehabilitative catalyst and insole or midsole through section B–B' of FIG. 2 showing the domed shaped insert with 2 positioning and security ribs of FIG. 17.
Figure 19:
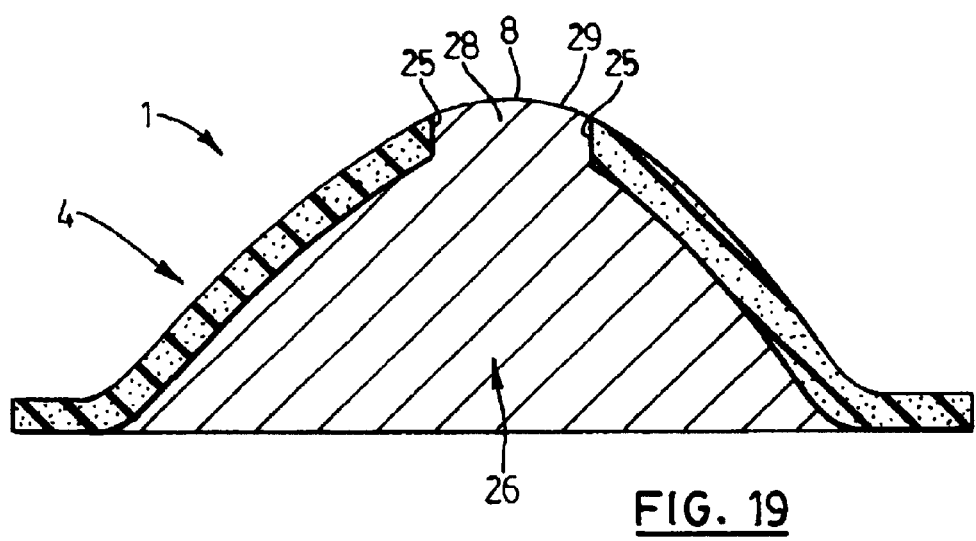
FIG. 19 is a frontal cross-sectional view of another embodiment of a arch rehabilitative catalyst and insole or midsole through section B–B' of FIG. 2 showing the domed shaped insert with a singular positioning and security rib.

FIGS. 17 through 19 illustrate a mechanism allowing a resilient member 26 of similar shape and design as the curvilinear geometric cavity 24 to be inserted into the curvilinear geometric cavity 24 without risk of the resilient member 26 deviating from its desired position. In this aspect of the disclosure apertures 29 are present in the catalyst 4 area of the device 1 which are aligned to receive positioning and security ribs 28 designed as an integral characteristic of the resilient member 26. The positioning and security ribs 28 have vertical sidewalls 27 which engage with the vertical sidewalls 25 and 31 of the insole or midsole to prevent any medial-lateral shifting or posterior-anterior shifting of the position of the resilient member 26.

Figures 23A, 23B:
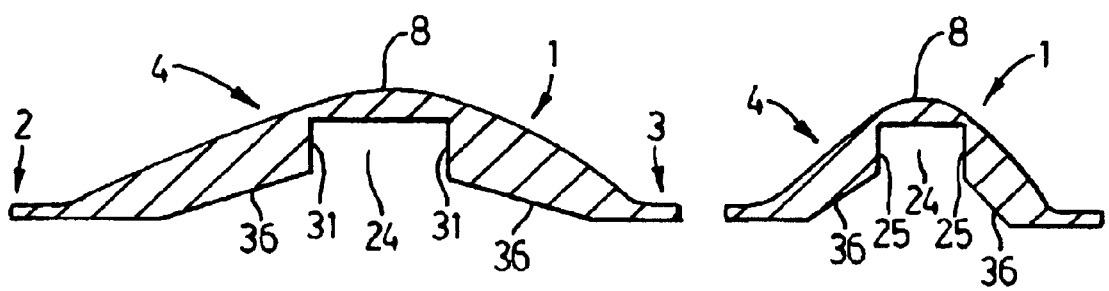
FIGS. 23a and 23b are frontal and sagittal plane views of further embodiment of the insole or midsole of the invention through sections A–A' and B–B' of FIG. 2 showing the positioning of a rectangular receptacle cavity in the arch rehabilitative catalyst with the cavity displaying a combination of vertical sidewalls and tapered sidewalls.

FIG. 23, reveals a preferred method of ensuring the presence of vertical sidewalls 31 and 25 in the geometric cavity 24 necessary to secure the resilient member 26 and providing an intrinsic cantilever effect. Vertical sidewalls 31 and 25 extend vertically downwardly from a maximum height, a predetermined distance, such that the distance is less than the maximum vertical distance from the inside maximum height of the geometric cavity 24 and the plantar supporting surface of the insole 1. The lower portion of the geometric cavity 24 is characterized by sidewalls 36 that are tapered. This design further utilizes the material properties of the insole body to provide a further cantilever effect as well as allowing a pumping action upon compression capable of circulating air throughout the in-shoe environment.

Figure 20:
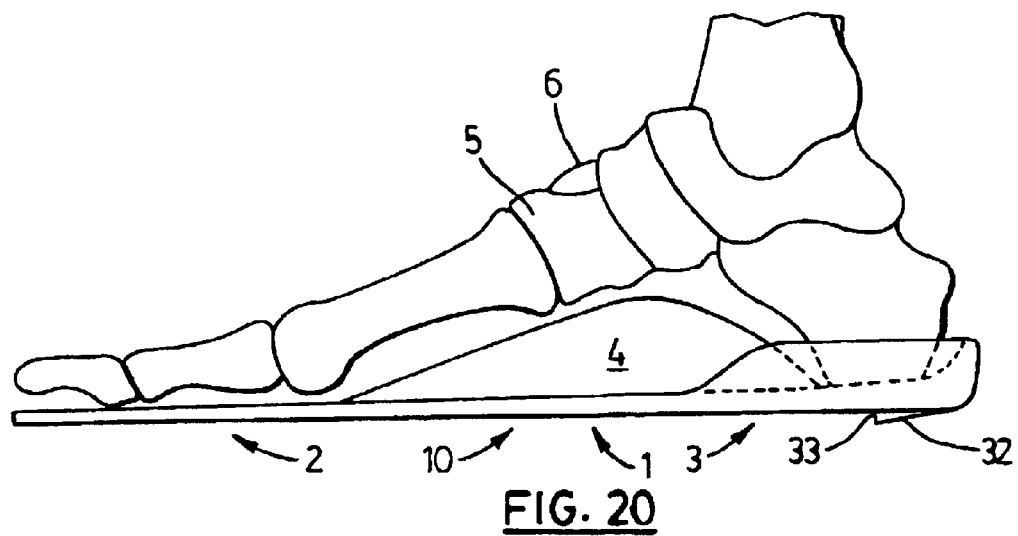
FIG. 20 is a medial sagittal view of another embodiment the invention showing the location of the arch rehabilitative catalyst relative to foot placement on the insole or midsole and the posterior heel skive.
Figure 21:
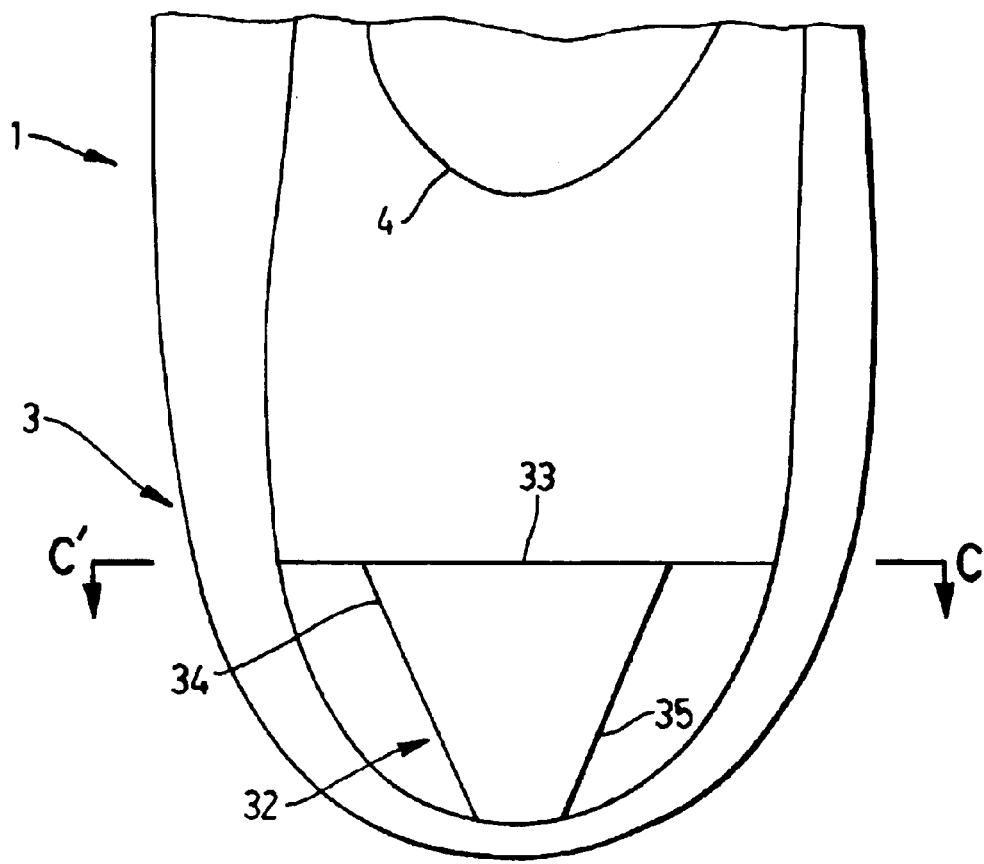
FIG. 21 is a view of the heel region of the insole or midsole device illustrating the location and characteristics of the tapered heel skive as shown in FIG. 20.
Figure 22:
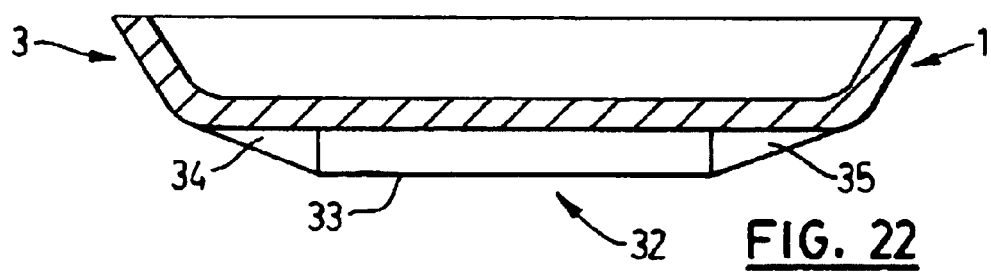
FIG. 22 is a frontal plane cross sectional view through section C–C' of FIG. 21 showing the geometric characteristics of the posterior heel skive.

In another aspect of the invention, device 1 as described, has a heel region 3 comprised of a tapered skive 32, as shown in FIG. 20, wherein the maximum skive thickness corresponds with the sagittal plane midline of the calcaneus and tapers by means of a sagittal angle to a level equal to the minimum thickness of the device 1 at the posterior most part of the device 1.

In this the tapered step 32 serves to reduce the velocity of the foot once it is planted on the ground at heal strike in normal heel to toe ambulation. This functions as a precaution by allowing the foot to be slowly lowered unto the catalyst 4. In doing so, any risk of impact related injury to the foots arch system is reduced, as well as increasing the initial comfort of the device 1 by allowing the pressure application to be more gradual.

The tapered skive provided for in other inventions are sufficiently able to perform effectively during an unidirectional ambulation but was designed such that it was not very effective in reducing the impact velocity when the foot was planted medially or laterally as in multi-directional sports. The purpose of slowly lowering the foot onto the catalyst 4 is still maintained during unidirectional ambulation through the sagittal plane taper created by the slope existing from the anterior most edge 33 and the posterior most edge of the device 1, and this effect can now also be provided for when the insole or midsole device 1 is used in multidirectional sports by the design addition of the medial skive 34 and the lateral skive 35. Again this serves to function as a precaution by allowing the foot to be slowly lowered unto the catalyst 4. In doing so, any risk of impact related injury to the foots arch system is reduced, as well as increasing the initial comfort of the insole or midsole 1 by allowing the pressure application to be more gradual. A non-symmetric altering of the medial and lateral skive 34 and 35 such that their angulations are different can be desirable for the design and creation of sport specific insole or midsoles.

Figure 24:
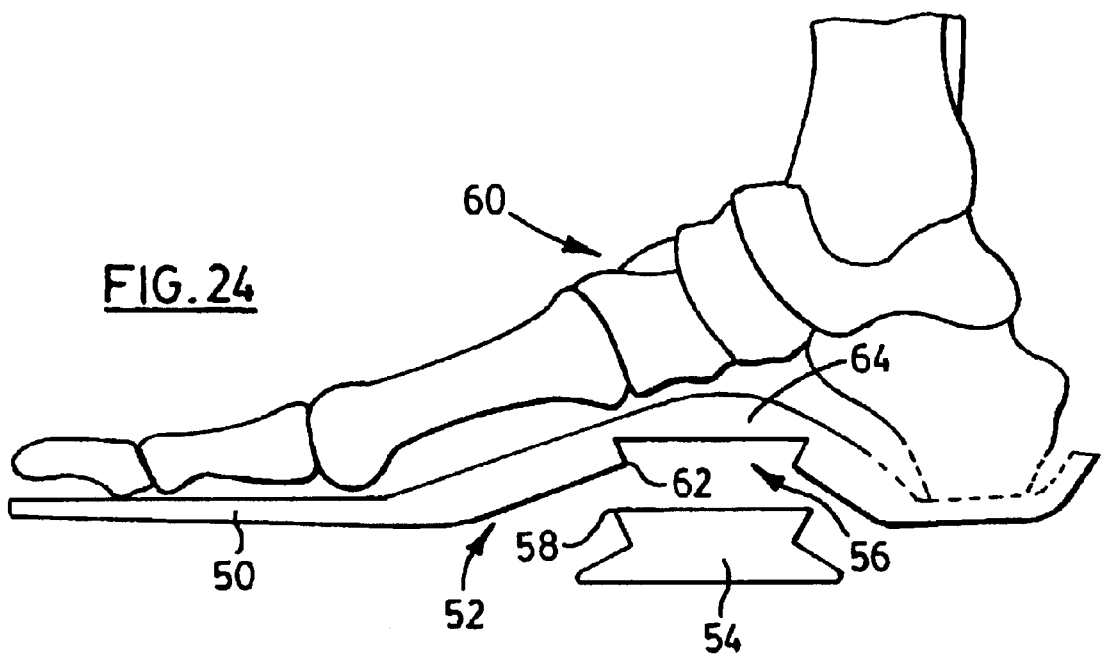
FIG. 24 is a sagittal plane cross-sectional view of another embodiment of an insole through section A–A' of FIG. 2 illustrating a foot positioned dorsal top, the insole having a cavity with an undercut opening and an insert having a geometry matching the cavity.

FIGS. 24 through 30 illustrate further embodiments of the present invention differing principally in insole/cavity configuration but in some cases also incorporating further therapeutic features. In FIG. 24, an insole 50 is provided having a cavity 52 for receiving an insert 54. The cavity 52 and insert 54 are provided with cooperating engagement means, 56 and 58 respectively, for securing the insert to the insole. The cooperating engagement means includes detent means in the form of an enlarged end 58 which is insertable through a narrower opening 62 in a catalyst portion 64 of the insole 50. This configuration requires resilient deformation of at least one of the insert 54 and catalyst 64 for insertion or removal and accordingly acts as detent means for resisting separation of the insert 54 from the insole 50 and lateral shifting therebetween.

Although the illustrations show a receptacle 56 in the catalyst and an enlarged end 58 on the insole, the reverse configuration would likely function equally well.

Figure 25B:
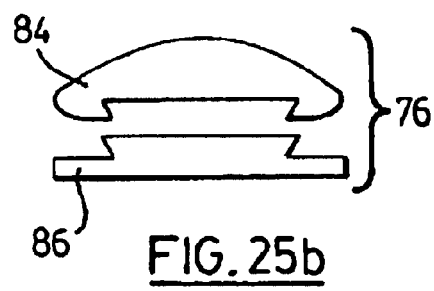
FIG. 25b illustrates the insert of FIG. 25a having a further stiffening component.
Figure 25A:
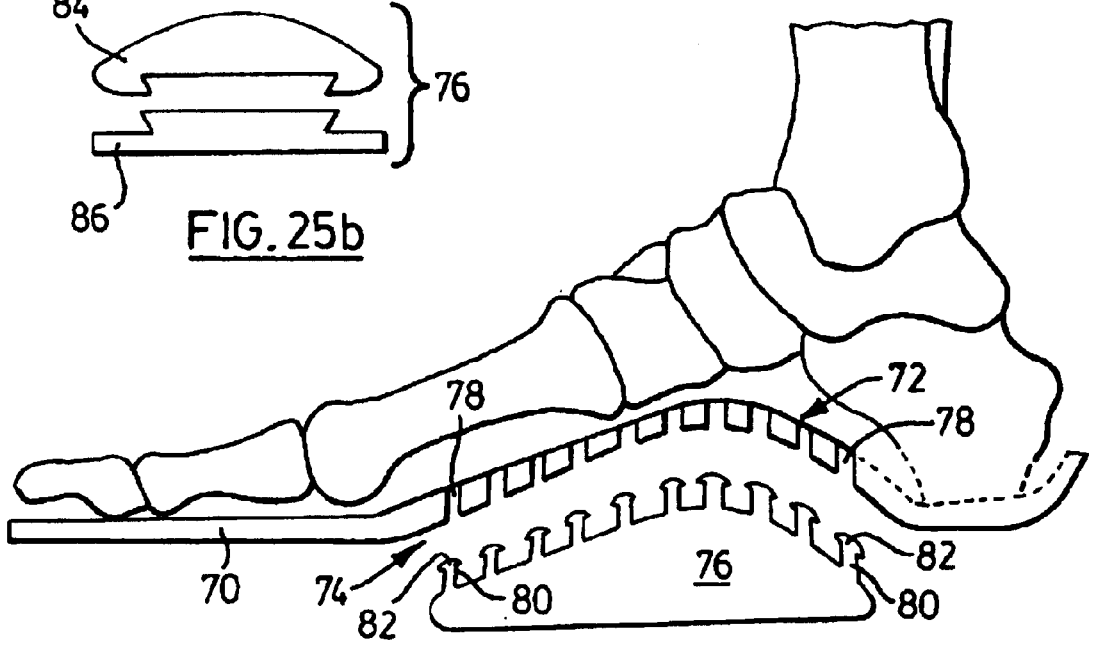
FIG. 25a is a sectional view illustrating a further embodiment in which the insert has protruding pillar heads.

FIG. 25a illustrates an insole 70 having a catalyst 72 having a recess 74 for receiving a catalyst 76. Cooperating engagement means in the form of apertures 78 through the catalyst and projections 80 from the insert having enlarged ends 82 are provided. The projections 80 register with the apertures 78 to allow insertion therethrough. The enlarged ends 82 act as a detent to prevent withdrawal of the projections 80 after insertion. The enlarged ends 82 deform resiliently in order to enable insertion.

As an added feature to the FIG. 25a embodiment, the projections 80 may incorporate a reflexology or massage component by having the enlarged ends 80 (which are at the distal end of the projections 80) line up with specific organ reference points from the field of reflexology. A reflexology chart may be consulted to determine the layout.

FIG. 25b illustrates an alternate embodiment of the insert 76 which may be applied to other of the inserts illustrated herein. In this arrangement, the insert 76 is of two components, an upper component 84 and a lower component 86. Either of these components can be made of different densities and components exchanged to vary the overall stiffness as part of an overall rehabilitative program.

FIG. 26a and 26b illustrate an insole 90 having a cavity 92 for removably accommodating an insert made up of parts 94 and 100. Part 94 has an enlarged end 98 from which depends a resilient column 95. The enlarged end 98 is received within a receptacle 96 of similar shape within the insole 90. The column 95 is received within a recess 102 within the component 100, the latter having a ring or cup-like shape. The component 100 closely surrounds at least part of the column 95 in order to resist resilient deformation of the column in a lateral direction thereby enhancing the stiffness of the column 95, and in turn determining the overall stiffness of the insert 94, 100.

The two-part insert 94 and 100 makes it possible to vary the stiffness without having to remove and replace the entire assembly. This may be accommodated by having different components 100 with different sized openings 102, different heights or different resiliencies which will affect the amount by which the component 100 can resist resilient deformation of the other component 94. In order to prevent the component 100 from riding up the column 95, a cup-shaped configuration might be desirable. Alternatively, if the component 94 diverges outwardly above the column 95, as illustrated in FIGS. 26a and 26b, the outward divergence should prevent riding up of the component 100 and accordingly a ring-like configuration may be adopted.

FIGS. 27a and 27b illustrate the use of mating strips of hook and loop fastener, 112 and 114 to retain an insert 116 within a cavity 118 of an insole 110. The FIG. 27b configuration further includes vertical walls 120 and 122 in the cavity 118 which register with respective corresponding vertical walls 124 and 126 on the insert 116 to resist lateral shifting therebetween.

Unlike adhesives which have proven in the past to be either too strong or too weak, and are generally not reusable with the same degree of adhesion, the mating strips 112 and 114 of hook and loop fastener will provide a satisfactory amount of securement without damage to the components upon removal and reusability without significant change in the securement capabilities.

FIG. 28a illustrates an insole 120 and an insert 122 similar to that illustrated and described above with respect to FIG. 25a. FIG. 28b is a perspective view from above the insole 120.

The insole 120 includes projections 124 having enlarged ends 126 which are received within receptacles 128 extending through the insole 120. As discussed above, the location and placement of the projections 124 and enlarged ends 128 may be such as to correspond to a reflexology chart. In addition, magnetic strips 130 may be provided between the insole 120 and the insert 122 to introduce an additional holistic therapy (magnetism) to the foot strengthening benefits of the insole 120.

It will be appreciated that opposite pole magnets might be used in lieu of the mating strips of hook and loop fastener, 112 and 114, in the FIG. 27b embodiment to provide both securement of the insert 116 to the insole 110 and as well introduce magnetism to the insole 110.

FIGS. 29a and 29b illustrate an arrangement similar to that illustrated and described above with respect to FIGS. 26b and 26a. An insole 140 in FIG. 29a has a resilient column 142 extending downwardly from a catalyst 141 through a cavity 146. Like the FIGS. 26a and 26b embodiment, a detachable ring member 144 is provided which has a receptacle 148 for receiving a lower-most end 150 of the column 142. The ring member 144 resists resilient deformation of the column 142 in a lateral direction thereby enhancing the stiffness of resilient column. The ring member 144 may be substituted for different ring members having different geometries and/or stiffnesses to vary the amount of resistance to lateral deformation thereby varying the overall stiffness of the resilient column 142.

Figure 30:
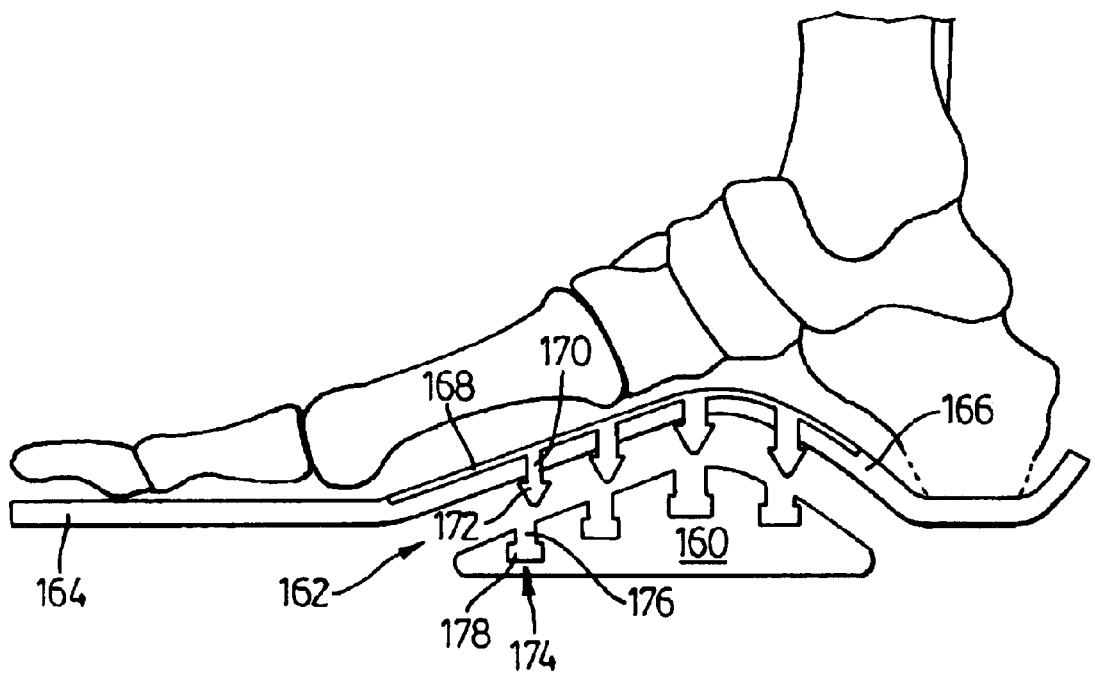
FIG. 30 illustrates an insole having an outer layer extending through the insole for engaging the insert.

FIG. 30 illustrates a further arrangement for securing an insert 160 within a cavity 162 of an insole 164. The insole 164 has a catalyst 166 and an outer cover 168 over the catalyst 166. The outer cover 168 has at least one projection 170 which extends downwardly from the outer cover through the insole and has enlarged ends 172. The insole 160 is provided with receptacles 174 having a narrow opening 176 terminating in an enlarged chamber 178. The enlarged ends 172 are insertable through the narrow opening 176 and releasably detained within the enlarged chamber 178.

It is understood that the above embodiments are illustrative of the invention and can be varied or amended without departing from the scope of the invention as defined in the appended claims.

What is claimed is:

1. A rehabilitative insole device comprising:
   a substantially dome-shaped catalyst for interfacing with the plantar aspect of a human foot;
   said catalyst having an apex for aligning with a target area within said foot, said target area defined by the point of articulation of the lateral cuneiform, cuboid and navicular bones of the foot, to permit uninhibited triplanar pivoting of said foot about said target area;
   said catalyst having a maximum height at said apex of from 1% to 5% of the length of said foot, wherein the length of said foot corresponds substantially to the length of said rehabilitative insole device;
   said catalyst being resiliently deformable to apply an upwardly directed pressure to stimulate the Golgi tendon organ in said foot in response to downward pressure on said catalyst by said foot;
   said resilient member having a resilient deformability allowing said catalyst to deflect from between 40% and 100% of said maximum height in response to vertical forces of a person standing at rest being applied to said catalyst.

2. A rehabilitative insole device as claimed in claim 1 in combination with an insert wherein:
   said catalyst has a cavity for removably accommodating said insert which acts between said catalyst and an underlying surface to control said resilient deformability of said catalyst;
   said catalyst and said insert have cooperating engagement means for securing said insert to said insole; and
   said cooperating engagement means includes detent means for resisting separation of said insert from said insole and lateral shifting therebetween.

3. The rehabilitative insole and insert of claim 2 wherein:
   said detent means includes an enlarged end on one of said insert and said catalyst which is insertable through a narrower opening in the other of said insert and said catalyst.

4. The rehabilitative insole device and insert of claim 3 wherein:
   said enlarged end is provided on a distal end of at least one projection extending from a respective of said insert and said catalyst.

5. The rehabilitative insole device and insert of claim 4 wherein:
   said catalyst has an outer cover over said insole and said at least one projection extends from said outer cover through said insole.

6. The rehabilitative insole with insert of claim 2 wherein:
   said cooperating engagement means includes vertical walls on said insert which register with corresponding vertical walls on said receptacle to resist lateral shifting therebetween; and
   said detent means includes mating strips of hook and loop fastener secured t an inner lateral surface of said receptacle and an outer lateral surface of said insert.

7. The rehabilitative insole with insert device of claim 4 wherein:
   said projection is a resilient column depending from said catalyst through said receptacle; and
   said insert has a recess which closely surrounds at least part of said column to resist resilient deformation of said column in a lateral direction thereby enhancing the stiffness of said resilient column.

8. The rehabilitative insole with insert of claim 2 further comprising:

a magnetic material interspersed between said insole and said insert.

9. The rehabilitative insole with insert of claim 4 wherein:

said insert has a resilient column extending downwardly from said insole in said cavity;

said insert further has a detachable ring member for receiving said column and resisting resilient deformation of said column in a lateral direction thereby enhancing the stiffness of said resilient column.

10. The rehabilitative insole with insert of claim 2 wherein:

said cooperating engagement means are mating strips of hook and loop fastener secured to registering faces of said insert and said insole.

11. The rehabilitative insole with insert of claim 2 wherein:

said cooperating engagement mans includes respective strips of opposite pole magnetic material secured to registering faces of said insert and said insole.

12. The rehabilitative insole with insert of claim 11 wherein:

said cooperating engagement means further includes vertical walls on said insert which register with vertical walls on said receptacle to resist lateral shifting therebetween.

13. The rehabilitative insole and insert of claim 2 wherein:

said detent means includes a plurality of projections extending upwardly from the insert and terminating in enlarged ends;

said detent means further includes apertures through the catalyst for receiving the projections with the enlarged ends terminating above the catalyst once said insert is secured to the insole;

said apertures and projections are arranged in a pattern corresponding to reflexology points on said foot to apply reflexology therapy in response to downward pressure by said foot on said insole.

14. The rehabilitative insole and insert of claim 13 wherein:

a magnetic material is provided between said insole and said insert around said projections.

\* \* \* \* \*